United States Patent [19]

Hsia et al.

[11] Patent Number: 4,504,691

[45] Date of Patent: Mar. 12, 1985

[54] OLEFIN FRACTIONATION AND CATALYTIC CONVERSION SYSTEM

[75] Inventors: Chung-hweng Hsia, Matawan; Hartley Owen, Belle Mead; Bernard S. Wright, East Windsor, all of N.J.

[73] Assignee: Mobil Oil Corporation, New York, N.Y.

[21] Appl. No.: 616,376

[22] Filed: Jun. 1, 1984

Related U.S. Application Data

[63] Continuation-in-part of Ser. No. 508,959, Jun. 29, 1983, Pat. No. 4,471,147, and a continuation-in-part of Ser. No. 508,907, Jun. 29, 1983, Pat. No. 4,450,311.

[51] Int. Cl.[3] .................... C07C 2/02

[52] U.S. Cl. .................... 585/519; 585/533

[58] Field of Search .................... 585/519, 533

[56] References Cited

U.S. PATENT DOCUMENTS

| | | | |
|---|---|---|---|
| 4,182,922 | 1/1980 | Schick et al. | 585/517 |
| 4,444,988 | 4/1984 | Capsuto et al. | 585/415 |
| 4,456,779 | 6/1984 | Owen et al. | 585/415 |

*Primary Examiner*—Curtis R. Davis

*Attorney, Agent, or Firm*—Alexander J. McKillop; Michael G. Gilman; L. G. Wise

[57] ABSTRACT

An improved catalytic process for converting an olefinic feedstock comprising ethylene and $C_3+$ olefins to heavier liquid hydrocarbon product comprising the steps of:

(a) prefractionating the olefinic feedstock to obtain a gaseous stream rich in ethylene and a liquid stream containing $C_3+$ olefin;

(b) vaporizing and contacting the liquid stream from the prefractionating step with hydrocarbon conversion oligomerization catalyst in at least one exothermic catalytic reaction zone at elevated temperature and pressure to provide a heavier hydrocarbon effluent stream comprising heavy, intermediate and light hydrocarbons;

(c) flashing the effluent stream between the reaction zone and a first phase separation zone by reducing pressure of the effluent stream, thereby producing a first liquid effluent fraction rich in heavy hydrocarbons and a first effluent vapor stream containing intermediate and light hydrocarbons;

(d) condensing a portion of the first effluent vapor stream in a second phase separation zone to produce a second liquid effluent stream rich in intermediate boiling range hydrocarbons and a second vapor stream rich in light hydrocarbons;

(e) recycling at least a portion of the second liquid effluent stream as a liquid sorbent stream to prefractionating step (a);

(f) further reacting the recycled gasoline together with sorbed $C_3+$ olefin in the catalytic reactor system of step (b).

7 Claims, 1 Drawing Figure

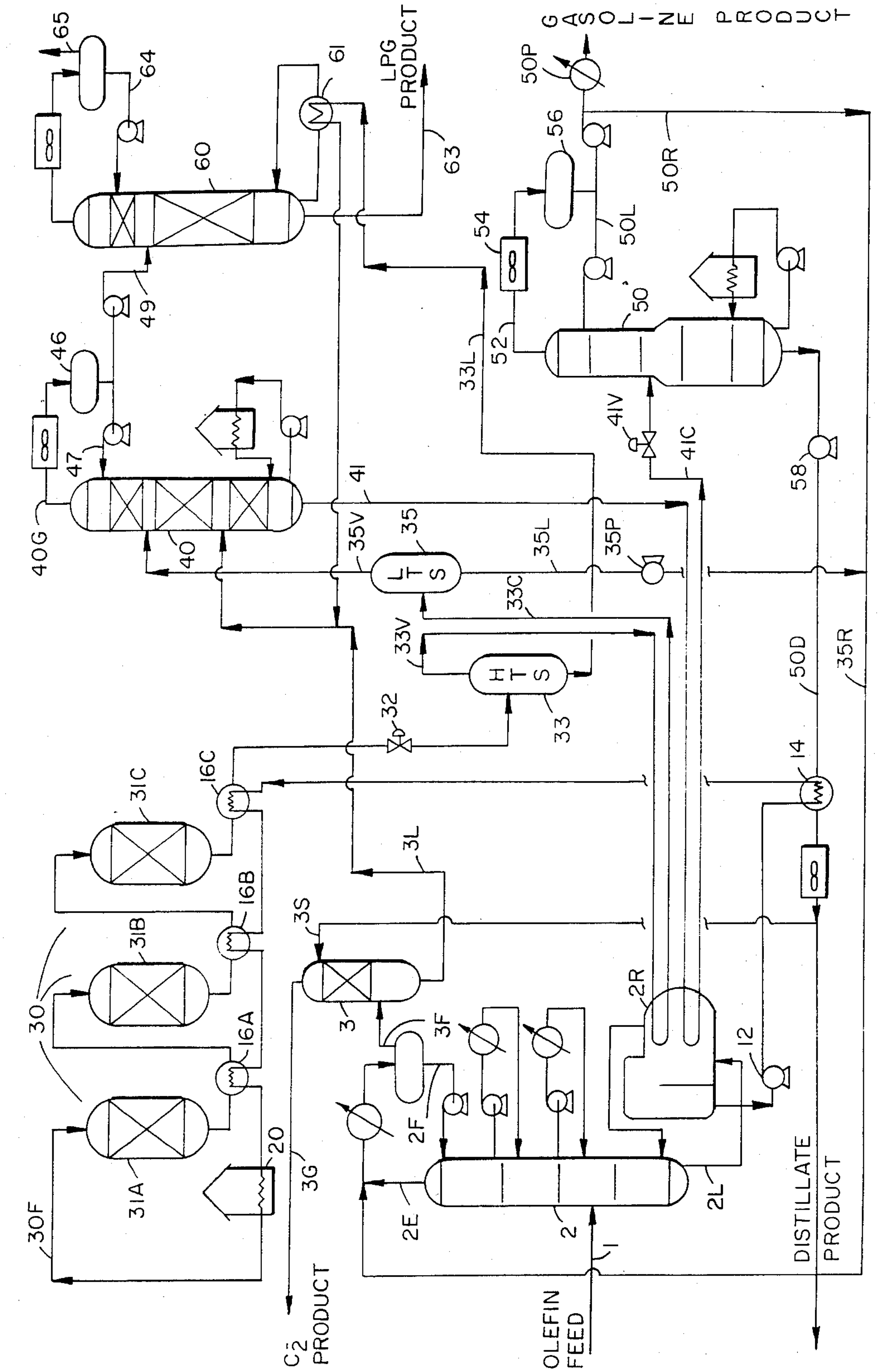
OLEFIN FEED
DISTILLATE PRODUCT
LPG PRODUCT
GASOLINE PRODUCT
PRODUCT
HTS
LTS

OLEFIN FRACTIONATION AND CATALYTIC CONVERSION SYSTEM

REFERENCE TO COPENDING APPLICATIONS

This application is a continuation-in-part of U.S. patent applications Ser. No. 508,959 and Ser. No. 508,907, filed June 29, 1983, now U.S. Pat. Nos. 4,471,147 and 4,450,311, respectively, incorporated herein by reference.

FIELD OF THE INVENTION

This invention relates to processes and apparatus for converting olefins to higher hydrocarbons, such as gasoline-range and/or distillate-range fuels. In particular it relates to techniques for operating a catalytic reactor system and feedstock fractionation system.

BACKGROUND OF THE INVENTION

Improved catalytic hydrocarbon conversion processes have created interest in utilizing olefinic feedstocks, such as petroleum refinery streams rich in lower olefins, for producing $C_5$+ gasoline, diesel fuel, etc. In addition to the basic work derived from ZSM-5 type zeolite catalyst research, a number of discoveries have contributed to the development of a new industrial process, known as Mobil Olefins to Gasoline/Distillate ("MOGD"). This process has significance as a safe, environmentally acceptable technique for utilizing refinery streams that contain lower olefins, especially $C_2$–$C_5$ alkenes. This process may supplant conventional alkylation units. In U.S. Pat. Nos. 3,960,978 and 4,021,502, Plank, Rosinski and Givens disclose conversion of $C_2$–$C_5$ olefins, alone or in admixture with paraffinic components, into higher hydrocarbons over crystalline zeolites having controlled acidity. Garwood et al have also contributed improved processing techniques to the MOGD system, as in U.S. Pat. Nos. 4,150,062, 4,211,640 and 4,227,992. The above-identified disclosures are incorporated herein by reference.

Conversion of lower olefins, especially propene and butenes, over H-ZSM-5 is effective at moderately elevated temperatures and pressures. The conversion products are sought as liquid fuels, especially the $C_5$+ aliphatic and aromatic hydrocarbons. Olefinic gasoline is produced in good yield by the MOGD process and may be recovered as a product or recycled to the reactor system for further conversion to distillate-range products.

As a consequence of the relatively low reactivity of ethylene with known zeolite oligomerization catalysts (about 10–30% conversion for H-ZSM-5), distillate-mode reactor systems designed to completely convert a large ethylene component of feedstock would require much larger size than comparable reactor systems for converting other lower olefins. Recycle of a major amount of ethylene from the reactor effluent would result in significant increases in equipment size. By contrast, propene and butene are converted efficiently, 75 to 95% or more in a single pass, under catalytic conditions of high pressure and moderate pressure used in distillate mode operation. In U.S. Pat. No. 4,433,185, Tabak employs a two stage conversion process, with interstage flashing of unconverted ethene and subsequent high severity ethene conversion.

Ethylene has substantial value as a feedstock for polymer manufacture or other industrial processes, and can be recovered economically. It has been found that an olefin-to-distillate process utilizing $C_2$–$C_4$ olefinic feedstock can be operated to prefractionate the feedstock for ethylene recovery and catalytic conversion of the $C_3$+ olefinic components.

Olefinic feedstocks may be obtained from various sources, including fossil fuel processing streams, such as gas separation units, cracking of $C_2$+ hydrocarbons, coal byproducts, alcohol conversion, and various synthetic fuel processing streams. Cracking of ethane and conversion of effluent is disclosed in U.S. Pat. No. 4,100,218 and conversion of ethane to aromatics over Ga-ZSM-5 is disclosed in U.S. Pat. No. 4,350,835. Olefinic effluent from fluidized catalytic cracking of gas oil or the like is a valuable source of olefins, mainly $C_3$–$C_4$ olefins, suitable for exothermic conversion according to the present MOGD process. It is an object of the present invention to provide a unique prefractionation system for recovery of valuable ethylene and economic operation of an integrated MOGD type reactor system.

SUMMARY OF THE INVENTION

A novel technique has been found for separating and catalytically converting olefins in a continuous process. Methods and apparatus are provided for converting a fraction of olefinic feedstock comprising ethylene and $C_3$+ olefins to heavier liquid hydrocarbon product. It is an object of this invention to effect conversion by prefractionating the olefinic feedstock to obtain a gaseous stream rich in ethylene and a liquid stream containing $C_3$+ olefin; vaporizing and contacting the liquid stream from the prefractionating step with hydrocarbon conversion oligomerization catalyst in at least one exothermic catalytic reaction zone at elevated temperature and pressure to provide a heavier hydrocarbon effluent stream comprising heavy, intermediate and light hydrocarbons; flashing the effluent stream between the reaction zone and a first phase separation zone by reducing pressure of the effluent stream, thereby producing a first liquid effluent fraction rich in heavy hydrocarbons and a first effluent vapor stress containing intermediate and light hydrocarbons; condensing a portion of the first effluent vapor stream in a second phase separation zone to produce a second liquid effluent stream rich in intermediate boiling range hydrocarbons and a second vapor stream rich in light hydrocarbons; recycling at least a portion of the second liquid effluent stream as a liquid sorbent stream to the prefractionating step; and further reacting the recycle stream together with sorbed $C_3$+ olefin in the catalytic reactor system.

A continuous process has been designed to achieve these objectives for an exothermic reactor system with efficient heat exchange, product recovery and recycle system. Advantageously, exothermic heat is recovered from at least a portion of the reactor effluent and utilized to heat one or more fractionation system liquid streams, such as a sorption prefractionator reboiler stream. In a preferred embodiment, this is achieved by exchanging heat between at least a portion of hot vapor effluent from a first phase separation zone and prefractionator bottoms liquid rich in $C_3$+ olefin in a prefractionator absorber reboiler loop.

Typically, the olefinic stock consists essentially of $C_2$–$C_6$ aliphatic hydrocarbons containing a major fraction of monoalkenes in the essential absence of dienes or other deleterious materials. The process may employ various volatile lower olefins as feedstock, with oligomerization of $C_3$+ alpha-olefins being preferred for either gasoline or distillate production. Preferably the olefinic feedstream contains about 50 to 75 mole % $C_3$–$C_5$ alkenes.

These and other objects and features of the novel MOGD system will be seen in the following description of the drawing.

DESCRIPTION OF THE DRAWING

The drawing is a schematic system diagram showing a process equipment and flow line configuration for a preferred embodiment.

DESCRIPTION OF PREFERRED EMBODIMENTS

Various olefinic and paraffinic light hydrocarbon streams may be involved in the reactor or fractionation subsystems. An olefinic feedstock, such as $C_2$–$C_4$ olefins derived from catalytic cracker (FCC) effluent, may be employed as a feedstock rich in ethene, propene, butenes, etc. for the process. The prefractionator/absorber unit separates the feedstock into a relatively pure ethene gas product and $C_3$+ liquid comprising the rich sorbent. Following reaction at elevated temperature and pressure over a shape selective catalyst, such as ZSM-5 or the like, the reactor system effluent is fractionated in a series of phase separators and distillation towers. In the examples herein fractionation sub-system has been devised to yield three main product streams—LPG (mainly $C_3$–$C_4$alkanes), gasoline boiling range hydrocarbons ($C_5$ to 330° F.) and distillate range heavier hydrocarbons (330° F+). However, the inventive concept applies to various separatory techniques for heavy, intermediate and light hydrocarbon products, as determined by relative molecular weight or carbon number. Optionally, all or a portion of the olefinic gasoline range hydrocarbons from the phase separation units may be recycled for further conversion to heavier hydrocarbons in the distillate range. This may be accomplished by combining the recycled intermediate range hydrocarbons with $C_3$+ olefin feedstock in the prefractionation step prior to heating the combined streams.

Process conditions, catalysts and equipment suitable for use in the MOGD process are described in U.S. Pat. Nos. 3,960,978 (Givens et al), 4,021,502 (Plank et al), and 4,150,062 (Garwood et al). Hydrotreating and recycle of olefinic gasoline are disclosed in U.S. Pat. No. 4,211,640 (Garwood and Lee). Other pertinent disclosures include U.S. Pat. No. 4,227,992 (Garwood and Lee) and U.S. patent application Ser. No. 488,834, filed Apr. 26, 1983 (Owen et al.) , now U.S. Pat. No. 4,456,779 relating to catalytic processes for converting olefins to gasoline/distillate. The above disclosures are incorporated herein by reference.

CATALYST

The catalytic reactions employed herein are conducted, preferably in the presence of medium pore silicaceous metal oxide crystalline catalysts, such as acid ZSM-5 type zeolites catalysts. These materials are commonly referred to as aluminosilicates or porotectosilicates; however, the acid function may be provided by other tetrahedrally coordinated metal oxide moieties, especially Ga, B, Fe or Cr. Commercially available aluminosilicates such as ZSM-5 are employed in the operative embodiments; however, it is understood that other silicaceous catalysts having similar pore size and acidic function may be used within the inventive concept.

The catalyst materials suitable for use herein are effective in oligomerizing lower olefins, especially propene and butene-1 to higher hydrocarbons. The unique characteristics of the acid ZSM-5 catalyts are particularly suitable for use in the MOGD system. Effective catalysts include those zeolites disclosed in U.S. patent application Ser. No. 390,099 filed Jun. 21, 1982 (Wong and LaPierre) , now U.S. Pat. No. 4,430,516, and application Ser. No. 408,954 filed Aug. 17, 1982 (Koenig and Degnan), now U.S. Pat. No. 4,465,884 which relate to conversion of olefins over large pore zeolites. A preferred catalyst material for use herein is an extrudate (1.5 mm) comprising 65 weight % HZSM-5 and 35% alumina binder, having an acid cracking activity ($\alpha$) of about 160 to 200.

The members of the class of crystalline zeolites for use in this invention are characterized by a pore dimension greater than about 5 Angstroms, i.e., it is capable of sorbing paraffins having a single methyl branch as well as normal paraffins, and it has a silica to alumina mole ratio of at least 12.

Although such crystalline zeolites with a silica to alumina mole ratio of at least about 12 are useful, it is preferred to use zeolites having higher ratios of at least about 30. In some zeolites, the upper limit of silica to alumina mole ratio is unbounded, with values of 30,000 and greater.

The members of the class of zeolites for use herein are exemplified by ZSM-5, ZSM-5/ZSM-11 intermediate, ZSM-11, ZSM-22, ZSM-23, ZSM-35, ZSM-38, ZSM-48 and other similar materials. U.S. Pat. No. 3,702,886 describing and claiming ZSM-5 is incorporated herein by reference. Also, U.S. Pat. No. Re. 29,948 describing and claiming a crystalline material with an X-ray diffraction pattern of ZSM-5, is incorporated herein by reference as is U.S. Pat. No. 4,061,724 describing a high silica ZSM-5 referred to as "silicate" in such patent. The ZSM-5/ZSM-11 intermediate is described in U.S. Pat. No. 4,229,424. ZSM-11 is described in U.S. Pat. No. 3,709,979. ZSM-23 is described in U.S. Pat. No. 4,076,842. ZSM-35 is described in U.S. Pat. No. 4,016,245. ZSM-38 is described in U.S. Pat. No. 4,046,859. The entire contents of the above identified patents are incorporated herein by reference. ZSM-48 is more particularly described in U.S. patent application Ser. No. 343,131 filed Jan. 27, 1982, now U.S. Pat. No. 4,375,573 the entire contents of which are incorporated herein by reference.

The zeolites used in additive catalysts in this invention may be in hydrogen form or they may be base exchanged or impregnated to contain a rare earth cation complement. Such rare earth cations comprise Sm, Nd, Pr, Ce and La. It is desirable to calcine the zeolite after base exchange.

The catalyst and separate additive composition for use in this invention may be prepared in various ways. They may be separately prepared in the form of particles such as pellets or extrudates, for example, and simply mixed in the required proportions. The particle size of the individual component particles may be quite small, for example from about 10 to about 150 microns, when intended for use in fluid bed operation, or they may be as large as up to about 1–10 mm for fixed bed operation. The components may be mixed as powders and formed into pellets or extrudate, each pellet containing both components in substantially the required proportions. It is desirable to incorporate the zeolite component of the separate additive composition in a matrix. Such matrix is useful as a binder and imparts greater resistance to the catalyst for the severe temperature, pressure and velocity conditions encountered in many cracking processes. Matrix materials include both synthetic and natural substances. Such substances include clays, silica and/or metal oxides. The latter may be either naturally occurring or in the form of gelatinous precipitates, sols or gels including mixtures of silica and metal oxides. Frequently, zeolite materials have been incorporated into naturally occurring clays, e.g. bentonite and kaolin.

A particularly advantageous form of the catalyst is an extruded pellet having a diameter of about 1-3 mm, made by mixing steamed zeolite crystals e.g. silica:alumina=70:1-500:1 with α-alumina monohydrate in a proportion of about 2:1 and calcining the formed material to obtain an extrudate having a void fraction of about 30-40%, preferably about 36%.

Referring to the drawing, olefinic rich feedstock is supplied to the plant through fluid conduit 1 under steady stream conditions. The olefins are separated in prefractionator 2 to recover an ethylene-rich stream 2E and liquid hydrocarbon stream 2L containing $C_3^+$ feedstock components. This $C_3^+$ feedstream is pressurized by pump 12 and then sequentially heated by passing through indirect heat exchange units 14, 16, and furnace 20 to achieve the temperature for catalytic conversion in reactor system 30, including plural reactor vessels 31A, B, C, etc.

The reactor system section shown consists of three downflow fixed bed, series reactors on line with exchanger cooling between reactors. The reactor configuration allows for any reactor to be in any position, A, B or C. The reactor in position A has the most aged catalyst and the reactor in position C has freshly regenerated catalyst. The cooled reactor effluent is separated by the high temperature separator (HTS) 33 and low temperature separator (LTS) 35 into light, intermediate and heavy range hydrocarbons. The intermediate range hydrocarbons are recycled to the inlet of the reactor in position A. The light and heavy hydrocarbons are further fractionated in the debutanizer 40 to provide lower aliphatic liquid and then in splitter unit 50, which not only separates the debutanizer bottoms into gasoline and distillate products, but provides additional liquid intermediate range hydrocarbon recycle.

The recycle is not only necessary to produce the proper distillate quality and yield but also limits the exothermic rise in temperature across each reactor to less than about 30° C. Change in recycle flow rate is intended primarily to compensate for gross changes in the feed non-olefin flow rate. As a result of preheat, the liquid recycle is substantially vaporized by the time it reaches the reactor inlet. The following is a description of the process flow in detail.

Sorbed $C_3^+$ olefin combined with olefinic gasoline is pumped up to system pressure by pump 12 and is combined with intermediate range hydrocarbon recycles 35L and 50R after these streams have been pumped up to system pressure. The combined stream ($C_3^+$ feed plus recycle) after preheat is routed to the inlet 30F of the reactor 31A of system 30. The combined stream (herein designated as the reactor feedstream) is first preheated against the effluent in exchanger 16C (reactor feed/position C reactor effluent exchanger), then against the effluent from the reactor in position B, in exchanger 16B (reactor feed/position B reactor effluent exchanger) and then against the effluent from the reactor in position C in exchanger 16C (reactor feed/position C reactor effluent exchanger). In the furnace 20, the reactor feed is heated to the required inlet temperature for the reactor in position A.

Because the reaction is exothermic, the effluents from the reactors in the first two positions A, B are cooled to the temperature required at the inlet of the reactors in the last two positions, B, C, by preheating the reactor feed. Temperature control is accomplished by allowing part of the reactor effluents to bypass exchangers 16A and 16B.

After heating part of fractionator 2 bottoms in reboiler 2R, the high temperature separator overhead is routed to the low temperature separator. Both high temperature separator bottoms, 33L after heating the deethanizer 60 bottoms in deethanizer reboiler 61, and the low temperature separator overhead, 35V enter on separate stages the debutanizer, which is operated at a pressure which completely condenses the debutanizer tower overhead 40G by cooling in condenser 44. The liquid from debutanizer overhead accumulator 46 provides the tower reflux 47, and feed to the deethanizer 60, which, after being pumped to the deethanizer pressure by pump 49 is sent to the deethanizer 60. The deethanizer accumulator overhead 35 is routed to the fuel gas system. The accumulator liquid 64 provides the tower reflux. The bottoms stream 63 (LPG product) may be sent to an unsaturated gas plant or otherwise recovered.

Under temperature control of the bottom stage of the sorption fractionator 2, the additional energy required for reboiling is provided by at least part of the debutanizer 41 bottom in the reboiler 2R. The bottoms stream 41 from the debutanizer 40 is sent then to the splitter, 50 which splits the $C_5^+$ material into $C_5$-330° F. gasoline (overhead liquid product and recycle) and 330° F.+ distillate (bottoms product). The splitter tower overhead stream 52 is totally condensed in the splitter tower overhead condenser 54. The liquid from the overhead accumulator 56 provides the tower reflux 50L, the gasoline product 50P and the make-up gasoline recycle 50R under flow control and pressurized for recycle. After being cooled in the gasoline product cooler 50P, the gasoline product is sent to the gasoline pool. The splitter bottoms fraction is pumped to the required pressure pump 58 and then preheats the reactor feed stream in exchanger 14. Finally, the distillate product 50D is cooled to ambient temperature before being hydrotreated to improve its cetane number.

From an energy conservation standpoint, it is advantageous to reboil the prefractionator bottoms 2L using hot effluent vapor and debutanizer bottoms liquid. A kettle reboiler 42 containing 2 U-tube exchangers 43 in which these streams are circulated is a desirable feature of the system. Liquid from the bottom stage of sorption fractionator 2 is circulated in the shell side.

The product fractionation units 40, 50, and 60 may be a tray-type design or packed column. The splitter distillation tower 50 is preferably operated at substantially atmospheric pressure to improve separation and to avoid excessive bottoms temperature, which might be deleterious to the distillate product. The fractionation equipment and operating techniques are substantially similar for each of the major stills 40, 50, 60, with conventional plate design, reflux and reboiler components. The fractionation sequence and heat exchange features of the present system are operatively connected in an efficient MOGD system to provide significant economic advantages.

MOGD operating modes may be selected to provide maximum distillate product by gasoline recycle and optimal reactor system conditions. Operating examples are given for distillate mode operation, utilizing as the olefinic feedstock a pressurized stream olefinic feedstock (about 1200 kPa) comprising a major weight and mole fraction of $C_3^=/C_4^=$. The adiabatic exothermic oligomerization reaction conditions are readily optimized at elevated temperature and/or pressure to increase distillate yield or gasoline yield as desired, using H-ZSM-5 type catalyst. Particular process parameters such as space velocity, maximum exothermic temperature rise, etc. may be optimized for the specific oligomerization catalyst employed, olefinic feedstock and desired product distribution.

DISTILLATE MODE REACTOR OPERATION

A typical distillate mode multi-zone reactor system employs inter-zone cooling, whereby the reaction exotherm can be carefully controlled to prevent excessive temperature above the normal moderate range of about 190° to 315° C. (375°-600° F.).

Advantageously, the maximum temperature differential across any one reactor is about 30° C. (°TΔ50° F.) and the space velocity (LHSV based on olefin feed) is about 0.5 to 1. Heat exchangers provide inter-reactor cooling and reduce the effluent to fractionation temperature. It is an important aspect of energy conservation in the MOGD system to utilize at least a portion of the reactor exotherm heat value by exchanging hot reactor effluent from one or more reactors with the reactor feed. Optional heat exchangers may recover heat from the effluent stream prior to fractionation. Gasoline from the recycle conduit is pressurized by pump means and combined with feedstock, preferably at a mole ratio of about 1-2 moles per mole of olefin in the feedstock. It is preferred to operate in the distillate mode at elevated pressure of about 4200 to 7000 kPa (600-1000 psig).

The reactor system contains multiple downflow adiabatic catalytic zones in each reactor vessel. The liquid hourly space velocity (based on total fresh feedstock) is about 1 LHSV. In the distillate mode the inlet pressure to the first reactor is about 5500 kPa (800 psig total), with an olefin partial pressure of at least about 1200 kPa. Based on olefin conversion of 50% for ethene, 95% for propene, 85% for butene-1 and 75% for pentene-1, and exothermic heat of reaction is estimated at 450 BTU per pound of olefins converted. When released uniformly over the reactor beds, a maximum ΔT in each reactor is about 30° C. In the distillate mode the molar recycle ratio for gasoline is 1.5 based on olefins in the feedstock.

SORPTION/PREFRACTIONATOR OPERATION

The prefractionation system is adapted to separate volatile hydrocarbons comprising a major amount of $C_2$-$C_4$ olefins, and typically contains 10 to 50 mole % of ethene and propene each. In the detailed examples herein the feedstock consists essentially of volatile aliphatic components as follows: ethene, 24.5 mole %, propene, 46%; propane, 6.5%; 1-butene, 15% and butanes 8%, having an average molecular weight of about 42 and more than 85 mole % olefins.

The gasoline sorbent is an aliphatic hydrocarbon mixture boiling in the normal gasoline range of about 50° to 165° C. (125° to 330° F.), with some amounts of $C_3$-$C_5$ alkanes and alkenes. Preferably, the total gasoline sorbent stream to feedstock weight ratio is greater than about 3:1; however, the content of $C_3^+$ olefinic components in the feedstock is a more preferred measure of sorbate or sorbent ratio. Accordingly, the process may be operated with a mole ratio of about 0.2 moles to about 10 moles of gasoline per mole of $C_3^+$ hydrocarbons in the feedstock, with optimum operation utilizing a sorbent:sorbate molar ratio about 1:1 to 1.5:1.

It is understood that the various process conditions are given for a continuous system operating at steady state, and that substantial variations in the process are possible within the inventive concept. In the detailed examples, metric units and parts by weight are employed unless otherwise specified.

Olefinic feedstock is introduced to the system through a feedstock inlet 1 connected between stages of a fractionating sorption tower 2 wherein gaseous olefinic feedstock is contacted with liquid sorbent in a vertical fractionation column operating at least in the upper portion thereof in countercurrent flow. Effectively this unit is a $C_2/C_3^+$ splitter. Design of sorption equipment and unit operations are established chemical engineering techniques, and generally described in Kirk-Othmer "Encyclopedia of Chemical Technology" 3rd Ed. Vol. 1 pp. 53-96 (1978) incorporated herein by reference. In conventional refinery terminology, the sorbent stream is sometimes known as lean oil.

Sorption tower 2, as depicted, has multiple contact zones, with the heat of absorption being removed via interstage pump around cooling means. The liquid gasoline sorbent is introduced to the sorption tower through an upper inlet means above the top contact section. It is preferred to mix incoming liquid sorbent with outgoing splitter overhead ethylene-rich gas from upper gas outlet 2E and to pass this multi-phase mixture into an interstage phase separator, operatively connected between the primary sorption tower 2 and a secondary sponge absorber 3. Liquid sorbent from the separator is then pumped to the upper liquid inlet for countercurrent contact in a plate column or the like with upwardly flowing ethylene rich vapors. Liquid from the bottom of upper contact zone is pumped to a heat exchanger in an upper loop, cooled and returned to the tower above an intermediate contact zone, again cooled in lower loop, and returned to the tower above a lower contact zone, which is located below the feedstock inlet 1. Under tower design conditions of about 2100 kPa (300 psia), it is preferred to maintain liquid temperature of streams entering the tower from each liquid inlet at about 40° C. (100° F.). The lower contact zone provides further fractionation of the olefin-rich liquid. Heat is supplied to the sorption tower by removing liquid from the bottom via a reboiler loop, heating this stream in heat exchanger, and returning the reboiled bottom stream to the tower below the lower contact zone.

The liquid sorbate-sorbent mixture is withdrawn through bottom outlet 2L and pumped to storage or to olefins recovery or to reaction. This stream is suitable for use as a feedstock in an olefins oligomerization unit or may be utilized as fuel products. Ethylene rich vapor from the primary sorption tower is withdrawn via the interstage separator through conduit 3.

Distillate lean oil is fed to the top inlet 3 of sponge absorber 3 under process pressure at ambient or moderately warm temperature (e.g. 40° C.) and distributed at the top of a porous packed bed, such as Raschig rings, having sufficient bed height to provide multiple stages. The liquid rate is low; however, the sponge absorber permits sorption of about 25 wt. percent of the distillate weight in $C_3^+$ components sorbed from the ethylene-rich stream. This stream is recovered from bottom outlet 3L. It is understood that the sorbate may be recovered from mixture with the sorbent by fractionation and the sorbent may be recycled or otherwise utilized. High purity ethylene is recovered from the system through gas outlet 3G and sent to storage, further processing or conversion to other products.

The sorption towers depicted in the drawing employ a plate column in the primary tower and a packed column in the secondary tower, however, the fractionation equipment may employ vapor-liquid contact means of various designs in each stage including packed beds of Raschig rings, saddles or other porous solids or low pressure drop valve trays (Glitsch grids). The number of theoretical stages will be determined by the feedstream composition, liquid:vapor (L/V) ratios, desired recovery and product purity. In the detailed example herein, 17 theoretical stages were employed in the primary sorption tower and 8 stages in the sponge absorber, with olefinic feedstock being fed between the 7th and 9th stages of the primary sorption tower.

In general, as the flow rate of lean oil increases, the ethylene recovery decreases, while the purity increases. The data for the splitter/absorber combination show that the excellent results are obtained with a gasoline mole ratio of at least 1:1 (based on $C_3^+$ hydrocarbons). Such conditions will result in a $C_2^=$ recovery of greater than 98%. Purity of more than 91 mole % can be achieved with a gasoline mole ratio of at least 2:1.

A preferred sorbent source is olefinic gasoline and distillate produced by catalytic oligomerization according to U.S. Pat. No. 4,211,640 (Garwood and Lee) and U.S. patent application Ser. No. 488,834, filed Apr. 26, 1983 (Owen et al), incorporated herein by reference. The $C_3^+$ olefin and gasoline sorbate may be fed directly to such oligomerization process, with a portion of recovered gasoline and distillate being recycled to the sorption fractionation system herein.

The stream components of the olefinic feedstock and other main streams of the sorption/prefractionator unit and reactor feedstreams are set forth in Table I, based on parts by weight per 100 parts of feedstock.

TABLE I

| Component wt. % | Fresh Feed | Main Sorption Fract. | Gasoline Recycle | Sponge Absorber Feed | Sorption Reflux | Distillate Sorbent | Ethene Product | Sponge Sorber Bottoms | Reactor Inlet |
|---|---|---|---|---|---|---|---|---|---|
| $C_1$ | 0.0 | 0.0 | 0.0 | 0.0 | 0.0 | 0.0 | 0.0 | 0.0 | 0.0 |
| $C_2^=$ | 16.3 | 49.6 | 0.0 | 16.3 | 33.2 | 0.0 | 16.1 | 0.3 | 0.0 |
| $C_2$ | 0.0 | 0.1 | 0.0 | 0.0 | 0.0 | 0.0 | 0.0 | 0.0 | 0.0 |
| $C_3^=$ | 45.9 | 3.8 | 1.7 | 0.6 | 5.1 | 0.0 | 0.6 | 0.0 | 46.9 |
| $C_3$ | 6.8 | 3.8 | 6.3 | 1.0 | 9.3 | 0.0 | 1.0 | 0.1 | 12.1 |
| i-$C_4$ | 7.7 | 2.5 | 11.8 | 0.7 | 13.7 | 0.0 | 0.6 | 0.1 | 18.8 |
| $C_4^=$ | 20.0 | 0.3 | 1.7 | 0.1 | 1.9 | 0.0 | 0.1 | 0.0 | 21.7 |
| $NC_4$ | 3.3 | 1.3 | 8.5 | 0.4 | 9.6 | 0.0 | 0.3 | 0.1 | 11.4 |
| i-$C_5$ | 0.0 | 0.4 | 5.8 | 0.1 | 6.1 | 0.0 | 0.1 | 0.0 | 5.7 |
| $C_5^=$ | 0.0 | 0.8 | 12.7 | 0.2 | 13.4 | 0.0 | 0.1 | 0.1 | 12.4 |
| n-$C_5$ | 0.0 | 0.0 | 0.3 | 0.0 | 0.3 | 0.0 | 0.0 | 0.0 | 0.4 |
| 125–330° F. | 0.0 | 1.3 | 209.6 | 0.4 | 210.6 | 0.06 | 0.0 | 0.4 | 209.3 |
| 330° F.+ | 0.0 | 0.0 | 16.8 | 0.0 | 16.3 | 3.5 | 0.0 | 3.5 | 16.3 |
| Stream No. | 1 | 2E | 35R | 3F | 2F liq | 3S | 3G | 3L | 30F |

More than 98% of ethylene is recovered in the above example from the feedstock, and the gas product requires additional treatment to raise its purity from 91 mol % to polymer grade.

In the refining of petroleum or manufacture of fuels from fossil materials or various sources of hydrocarbonaceous sources, an olefinic mixture is often produced. For instance, in cracking heavier petroleum fractions, such as gas oil, to make gasoline or distillate range products, light gases containing ethene, propene, butene and related aliphatic hydrocarbons are produced. It is known to recover these valuable by-products for use as chemical feedstocks for other processes, such as alkylation, polymerization, oligomerization, LPG fuel, etc. Ethylene is particularly valuable as a basic material in the manufacture of polyethylene and other plastics, and its commercial value is substantially higher as a precursor for the chemical industry than as a fuel component. Accordingly, it is desirable to separate ethylene in high purity for such uses.

A typical byproduct of fluid catalytic cracking (FCC) units is an olefinic stream rich in $C_2$–$C_4$ olefins, usually in mixture with lower alkanes. Ethylene can be recovered from such streams by conventional fractionation means, such as cryogenic distillation, to recover the $C_2$ and $C_3^+$ fractions; however, the equipment and processing costs are high.

There are several reasons for not converting the ethylene to distillate and gasoline. The high pressure and low space velocity required for any significant conversion (on the order of 75 wt. %) would require a separate reactor train and at least one additional tower. This would substantially increase the capital cost of the unit. Converting the ethylene with the propylene/butylene stream would result in an ethylene conversion of about 20 wt. %. Additionally, the value of polymer grade ethylene may be much higher than the gasoline and distillate which would be produced if the ethylene were to be converted. Finally, there would be difficulty in scheduling the regeneration section to regenerate both the ethylene conversion and propylene/butylene conversion reactors.

While the invention has been described by specific examples and embodiments, there is no intent to limit the inventive concept except as set forth in the following claims.

What is claimed is:

1. An improved catalytic process for converting an olefinic feedstock comprising ethylene and $C_3^+$ olefins to heavier liquid hydrocarbon product comprising the steps of:

(a) prefractionating the olefinic feedstock to obtain a gaseous stream rich in ethylene and a liquid stream containing $C_3^+$ olefin;

(b) vaporizing and contacting the liquid stream from the prefractionating step with hydrocarbon conversion oligomerization catalyst in at least one exothermic catalytic reaction zone at elevated temperature and pressure to provide a heavier hydrocarbon effluent stream comprising heavy, intermediate and light hydrocarbons;

(c) flashing the effluent stream between the reaction zone and a first phase separation zone by reducing pressure of the effluent stream, thereby producing a first liquid effluent fraction rich in heavy hydrocarbons and a first effluent vapor stream containing intermediate and light hydrocarbons;

(d) condensing a portion of the first effluent vapor stream in a second phase separation zone to produce a second liquid effluent stream rich in intermediate boiling range hydrocarbons and a second vapor stream rich in light hydrocarbons;

(e) recycling at least a portion of the second liquid effluent stream as a liquid sorbent stream to prefractionating step (a);

(f) further reacting the recycled gasoline together with sorbed $C_3+$ olefin in the catalytic reactor system of step (b); and (g) exchanging heat between hot vapor from the first phase separation zone and prefractionator bottom liquid rich in $C_3+$ olefin in a prefractionator sorption reboiler loop, thereby partially condensing the first vapor stream.

2. A process for producing liquid comprised predominantly of distillate-range hydrocarbons according to claim 1, further comprising: reacting olefin-rich feedstock in a series of fixed bed adiabatic reactors at elevated pressure and at a temperature of about 190° C. to 315° C. with a maximum temperature rise of about 30° C. in each reactor; cooling each reactor effluent prior to further exothermic oligomerization; and heat exchanging at least one reactor effluent stream with the liquid prefractionation stream to vaporize sorbed hydrocarbons.

3. A process according to claim 2 wherein the catalyst consists essentially of acid ZSM-5 type zeolite.

4. The process of claim 1 further comprising the step of exchanging heat between $C_5+$ rich debutanizer bottom and at least a portion of prefractionator bottoms liquid rich in $C_3+$ olefins in an absorber prefractionator reboiler.

5. A catalytic process for converting an olefinic feedstock comprising lower olefins to heavier hydrocarbon product comprising the steps of:

prefractionating the olefinic feedstock in a stripper tower to obtain a light gaseous overhead stream and a liquid stream comprising olefinic sorbate;

contacting the liquid stream from the prefractionating step with shape selective zeolite oligomerization catalyst in at least one exothermic catalytic reaction zone at elevated temperature and pressure to provide a heavier hydrocarbon effluent stream comprising heavy, intermediate and light hydrocarbons;

flashing the effluent stream between the reaction zone and a phase separation zone by reducing pressure of the effluent stream, thereby producing a heavy liquid product stream rich in heavy hydrocarbons and a flashed effluent vapor stream containing lighter hydrocarbons;

separating and recovering a recycle stream rich in intermediate range hydrocarbons from the separation zone and pressurizing the recycle stream for recycle to the stripper tower absorbent.

6. The process of claim 5 wherein the oligomerization catalyst comprises a shape-selective medium pore crystalline aluminosilicate zeolite having a silica:alumina mole ratio of at least 12 and a constraint index of about 1 to 12.

7. The process of claim 6 wherein the catalyst comprises H-ZSM-5 having an acid cracking activity of about 160 to 200, and the olefinic feedstock comprises about 10 to 50 mole % ethylene and 10 to 50 mole % propene.

* * * * *